(12) United States Patent
Omote et al.

(10) Patent No.: US 8,767,918 B2
(45) Date of Patent: Jul. 1, 2014

(54) X-RAY SCATTERING MEASUREMENT DEVICE AND X-RAY SCATTERING MEASUREMENT METHOD

(75) Inventors: Kazuhiko Omote, Akiruno (JP); Boris Verman, Bloomfield, MI (US); Licai Jiang, Rochester Hills, MI (US)

(73) Assignee: Rigaku Corporation, Tokyo (JP)

( * ) Notice: Subject to any disclaimer, the term of this patent is extended or adjusted under 35 U.S.C. 154(b) by 348 days.

(21) Appl. No.: 13/266,842

(22) PCT Filed: Apr. 14, 2010

(86) PCT No.: PCT/JP2010/056642
§ 371 (c)(1),
(2), (4) Date: Oct. 28, 2011

(87) PCT Pub. No.: WO2010/125913
PCT Pub. Date: Nov. 4, 2010

(65) Prior Publication Data
US 2012/0051518 A1 Mar. 1, 2012

(30) Foreign Application Priority Data
Apr. 30, 2009 (JP) ................................ 2009-110657

(51) Int. Cl.
*G21K 1/06* (2006.01)
*G01N 23/201* (2006.01)

(52) U.S. Cl.
CPC ............... *G21K 1/06* (2013.01); *G01N 23/201* (2013.01)
USPC ..................... 378/86; 378/70; 378/84; 378/85

(58) Field of Classification Search
CPC .......... G01N 23/201; G01N 23/20008; G01N 2223/054; G01N 2223/052; G21K 1/06; G21K 2201/061; G21K 2201/064; G21K 1/062; G21K 2201/067
USPC .............................................. 378/70, 84–86
See application file for complete search history.

(56) References Cited

U.S. PATENT DOCUMENTS

| 4,242,588 A | 12/1980 | Silk et al. |
| 5,646,976 A | 7/1997 | Gutman |

(Continued)

FOREIGN PATENT DOCUMENTS

| DE | 299 24 462 U1 | 6/2003 |
| EP | 1 396 716 A2 | 3/2004 |

(Continued)

OTHER PUBLICATIONS

Bruker AXS Inc., General Area Detector Diffraction System (GADDS), 2005, User manual, Version 4.1.xx, 287 pages.*

(Continued)

*Primary Examiner* — Toan Ton
*Assistant Examiner* — John Corbett
(74) *Attorney, Agent, or Firm* — Birch, Stewart, Kolasch & Birch, LLP (57) ABSTRACT

A X-ray scattering measurement device and measurement method can measure, with high resolution, the intensity of X-rays which have undergone small-angle scattering and diffraction with reflection geometry and can easily and accurately measure a microstructure on the surface of a sample. The X-ray scattering measurement device is suitable for microstructural measurement on the surface of a sample includes an X-ray source that generates an X-ray; a first mirror and a second mirror that continuously reflect the generated X-ray; a sample stage that supports the sample; and a two-dimensional detector that detects the X-ray scattered on the surface of the sample. The first mirror focuses the generated X-ray onto the two-dimensional detector within a plane parallel to the surface of the sample, and the second mirror focuses the X-ray reflected by the first mirror onto the surface of the sample within a plane perpendicular to the surface of the sample.

16 Claims, 6 Drawing Sheets

(56) References Cited

U.S. PATENT DOCUMENTS

| | | |
|---|---|---|
| 5,799,056 A | 8/1998 | Gutman |
| 6,041,099 A | 3/2000 | Gutman et al. |
| 6,459,763 B1 | 10/2002 | Koinuma et al. |
| 6,990,177 B2 | 1/2006 | Fujinawa et al. |
| 2004/0066903 A1 | 4/2004 | Fujinawa et al. |
| 2006/0239405 A1* | 10/2006 | Verman et al. ............... 378/85 |
| 2006/0269045 A1 | 11/2006 | Jiang |
| 2008/0069302 A1* | 3/2008 | Jiang ............................ 378/86 |

FOREIGN PATENT DOCUMENTS

| | | |
|---|---|---|
| JP | 05-256800 A | 10/1993 |
| JP | 06-294899 A | 10/1994 |
| JP | 11-133191 A | 5/1999 |
| JP | 2000-155102 A | 6/2000 |
| JP | 2001-066398 A | 3/2001 |
| JP | 2001-153822 A | 6/2001 |
| JP | 2002-310947 A | 10/2002 |
| JP | 2003-215069 A | 7/2003 |
| JP | 2008-542751 A | 11/2008 |

OTHER PUBLICATIONS

Jiang et al. "Application of Multilayer Optics to X-Ray Diffraction Systems" The Rigaku Journal, Rigaku, dated Oct. 21, 2001, vol. 18, No. 2, p. 13-22.

* cited by examiner

X-RAY SCATTERING MEASUREMENT DEVICE AND X-RAY SCATTERING MEASUREMENT METHOD

TECHNICAL FIELD

The present invention relates to an X-ray scattering measurement device and an X-ray scattering measurement method suitable for microstructural measurement on the surface of a sample.

BACKGROUND ART

A large number of SEMs, AFMs and the like are used to locally evaluate, for example, nanodots formed on a surface and nanofabrication of a semiconductor device. On the other hand, as a complementary method of performing measurements on an average structure, grazing-incidence small-angle X-ray scattering (GISAXS), in which X-rays are irradiated to a surface at a grazing angle, the intensity of the X-ray scattering is analyzed and thus measurements are performed on the nanostructure of the surface, has been widely used in recent years because a powerful synchrotron source has been realized.

As a technology on such small-angle scattering, there is one (for example, see patent document 1) that achieves high resolution by forming the focal point of X-rays on a detector with an optical element. A two-dimensional small-angle X-ray camera disclosed in patent document 1 forms a well-defined two-dimensional beam by a combination of a small focus source and a two-dimensional multilayer optical element.

As a similar technology, there is disclosed a technology that uses a Kirkpatrick-Baez scheme to focus, with two mirrors, X-rays in the vicinity of a detector (for example see non-patent document 1). In non-patent document 1, there is also disclosed an optical system that arranges two mirrors side by side to focus X-rays.

On the other hand, with respect to small-angle scattering, a technology for forming the focal point of X-rays onto a sample is also disclosed (for example, see patent document 2). The device disclosed in patent document 2 converges X-rays in a horizontal direction with a first mirror, converges X-rays in a vertical direction with a second mirror, and focuses the X-rays to a 0.1 mm by 0.1 mm region on the sample.

RELATED ART DOCUMENTS

Patent Documents

Patent document 1: Japanese Unexamined Patent Application Publication (Translation of PCT Application) NO. 2008-542751
Patent document 2: Japanese Unexamined Patent Application Publication No. H05-256800

Non-patent Documents

Non-patent document 1: Licai Jiang, Boris Verman, Bonglea Kim, Yuri Platonov, Zaid Al-Mosheky, Rick Smith, Nick Grupido, "APPLICATION OF MULTILAYAR OPTICS TO X-RAY DIFFRACTION SYSTEMS", THE RIGAKU JOURNAL, RIGAKU, Oct. 21, 2001, Vol. 18, No. 2, P. 13-22

DISCLOSURE OF THE INVENTION

Problems to be Solved by the Invention

If the above-described evaluation of the nanostructure on the sample surface can be performed immediately after the fabrication of the device or the sample, it is effective in terms of convenience. In order to achieve this, a device is required that can be used in a laboratory with comparable quality of the small-angle scattering data that are measured by synchrotron source.

The devices disclosed in patent document 1 and non-patent document 1, however, improve the resolution of the detector by passing X-rays through the sample, and therefore they are not suitable for microstructural measurement on the sample surface. Even if this type of device is used in an optical system where X-rays are reflected on a sample and are focused onto a detector, a spot size is extended in an X-ray irradiation direction, and thus the resolution of is lowered on the detector. Although the device disclosed in patent document 2 focuses X-rays onto a sample, a spot size is extended on a detector, and thus a desired resolution cannot be obtained.

In view of the foregoing circumstances, the present invention has been made and has an object to provide an X-ray scattering measurement device and an X-ray scattering measurement method that can measure, with high resolution, the intensity of X-rays which have undergone small-angle scattering and diffraction with reflection geometry and that can easily and accurately measure a microstructure on the surface of a sample.

Means of Solving the Problems (1) To achieve the above object, the X-ray scattering measurement device according to the present invention is an X-ray scattering measurement device suitable for microstructural measurement on a surface of a sample, the device comprising: an X-ray source that generates an X-ray; a first mirror that reflects the generated X-ray; a second mirror that reflects the X-ray reflected by the first mirror; a sample stage that supports the sample to which the X-ray reflected by the second mirror is irradiated; and a two-dimensional detector that detects the X-ray scattered on the surface of the sample, wherein the first mirror focuses the generated X-ray onto the two-dimensional detector within a plane parallel to the surface of the sample, and the second mirror focuses the X-ray reflected by the first mirror onto the surface of the sample within a plane perpendicular to the surface of the sample.

Since, as described above, the X-ray scattering measurement device according to the present invention uses the second mirror to focus the X-ray on the surface of the sample, it is possible to minimize the extension of a spot size in an X-ray irradiation direction. Then, it is possible to perform measurements on reflection small-angle scattering without lowering resolution. It is possible to perform measurements on a two-dimensionally periodic surface microstructure by utilizing the diffraction of the X-ray. Thus, it is possible to accurately measure the microstructure of a nanometer size on the surface of the sample.

It is also possible to evaluate the shapes of a semiconductor devices and a magnetic recording media fabricated on the surface of a substrate. When the shrinking of device structures in the future, a method using light is considered to be close to a detection limit in principle due to the limit of wavelengths; however, with X-rays, it is possible to perform ultimate atomic-level measurements on structures without encountering such limitation. It is also possible to perform, in laboratories, measurements on much of GISAXS that is conventionally performed with synchrotron source; it is possible to easily obtain sufficient data comparable to data obtained with synchrotron source, immediately after the fabrication of a device or a sample without the sample being damaged; it is possible to utilize it to organize the production processes of various devices.

(2) The X-ray scattering measurement device according to the present invention is an X-ray scattering measurement device suitable for microstructural measurement on a surface of a sample, the device comprising: an X-ray source that generates an X-ray; a first mirror that reflects the generated X-ray; a second mirror that reflects the X-ray reflected by the first mirror; a sample stage that supports the sample to which the X-ray reflected by the second mirror is irradiated; and a two-dimensional detector that detects the X-ray scattered on the surface of the sample, wherein the first mirror focuses the generated X-ray onto the surface of the sample within a plane perpendicular to the surface of the sample, and the second mirror focuses the X-ray reflected by the first mirror onto the two-dimensional detector within a plane parallel to the surface of the sample.

Since, as described above, the X-ray is focused onto the surface of the sample within the plane perpendicular to the surface of the sample, it is possible to perform measurements on reflection small-angle scattering with high resolution. It is also possible to perform accurate measurements on a two-dimensionally periodic surface microstructure by utilizing the diffraction of the X-ray. As described above, with the X-ray, it is possible to measure the microstructure on the surface of the sample.

(3) The X-ray scattering measurement device according to the present invention further comprises a mirror support portion that arranges and integrally supports the first mirror and second mirror such that reflective surfaces thereof are perpendicular to each other, wherein the mirror support portion is provided so as to be able to rotate about two axes: an axis of rotation which changes a reflection angle of the X-ray by the first mirror and moves the second mirror in a direction perpendicular to an incident plane of the X-ray; and an axis of rotation which changes a reflection angle of the X-ray by the second mirror and moves the first mirror in a direction perpendicular to an incident plane of the X-ray. Thus, it is possible to independently adjust the first mirror and the second mirror; this makes it easier to adjust two mirrors having different focal positions.

(4) In the X-ray scattering measurement device according to the present invention, the second mirror, which focuses the X-ray reflected by the first mirror onto the surface of the sample within the plane perpendicular to the surface of the sample, can limit to 50 µm or less a spot size of the X-ray on the surface of the sample in a direction perpendicular to the surface of the sample. Thus, it is possible to reduce the extension of the spot size in an X-ray irradiation direction, to measure the intensity of X-ray scattering reflecting the microstructure formed on the surface of the sample with high resolution and to perform accurate measurements on the microstructure.

(5) In the X-ray scattering measurement device according to the present invention, the first mirror, which focuses the generated X-ray onto the detector within the plane parallel to the surface of the sample, adjusts a spot size of the X-ray on the detector such that the spot size is about 200 µm or about the pixel size of the detector in a direction parallel to the surface of the sample. Thus, it is possible to reduce the extension of the spot size of the X-ray on the detector in the direction parallel to the surface of the sample, to measure the intensity of X-ray scattering reflecting the microstructure formed on the surface of the sample with high resolution and to perform accurate measurements on the microstructure.

(6) In the X-ray scattering measurement device according to the present invention, the sample stage is provided so as to be rotatable to change an incident angel of the generated X-ray to the surface of the sample and to be rotatable within a plane of the surface of the sample.

Hence, a large number of diffraction peaks are detected from the diffracted X-ray that is obtained, from the periodic structure formed on the sample surface, by rotating the sample in an azimuth direction to satisfy the Bragg conditions, and thus it is possible to measure the pitch and the line width of the periodic structure with high accuracy. Moreover, it is possible to independently evaluate the sidewall angle and the roughness of a sidewall on the cross-sectional shape of the periodically formed structures. As described above, it is possible to accurately identify the features of the microstructure.

(7) In the X-ray scattering measurement device according to the present invention, the first mirror or second mirror is a multilayer mirror. Hence, the first or second mirror can change a d-spacing by the incident position of the X-ray. Thus, even when the incident angle is changed, it is possible to cause diffraction by adjusting the d-spacing. Consequently, in the case where the X-ray is focused by the first mirror onto the two-dimensional detector and the X-ray is focused by the second mirror onto the sample surface, it is possible to select only X-ray having the same wavelength as the characteristic X-ray (CuKα) and perform measurements with low background.

(8) In the X-ray scattering measurement device according to the present invention, the first mirror or second mirror is formed with a crystal plate. Thus, the first mirror or second mirror can extract only Kα1 X-rays, for example. Consequently, it is possible to produce X-rays having high monochromaticity and further perform detection with high resolution.

(9) The X-ray scattering measurement device according to the present invention includes a pair of collimation blocks in an X-ray passage portion between the second mirror and the sample. Thus, it is possible to accurately block the X-ray to enhance the accuracy of the collimation.

(10) The X-ray scattering measurement method according to the present invention is an X-ray scattering measurement method suitable for microstructural measurement on a surface of a sample, the method comprising the steps of: reflecting an X-ray generated by an X-ray source with a first mirror; reflecting the X-ray reflected by the first mirror with a second mirror; making the X-ray reflected by the second mirror incident on the sample; and detecting the X-ray scattered on the surface of the sample with a two-dimensional detector, wherein the first mirror focuses the generated X-ray and the second mirror focuses the X-ray reflected by the first mirror, and a focusing position within a plane parallel to the surface of the sample is set on the two-dimensional detector and a focusing position within a plane perpendicular to the surface of the sample is set on the surface of the sample, and thus an X-ray scattered at a small angle on the surface of the sample is detected.

Since, as described above, the X-ray is focused onto the surface of the sample within the plane perpendicular to the surface of the sample, it is possible to perform measurements on reflection small-angle scattering with high resolution. It is also possible to perform accurate measurements on the two-dimensionally periodic surface microstructure by utilizing the diffraction of the X-ray. As described above, with the X-ray, it is possible to perform measurements on the microstructure on the surface of the sample.

(11) The X-ray scattering measurement method according to the present invention is an X-ray scattering measurement method suitable for microstructural measurement on a surface of a sample, the method comprising the steps of: reflecting an X-ray generated by an X-ray source with a first mirror; reflecting the X-ray reflected by the first mirror with a second mirror; making the X-ray reflected by the second mirror incident on the sample; and detecting the X-ray scattered on the surface of the sample with a two-dimensional detector, wherein the first mirror focuses the generated X-ray and the second mirror focuses the X-ray reflected by the first mirror, and a focusing position within a plane parallel to the surface of the sample is set on the two-dimensional detector and a focusing position within a plane perpendicular to the surface of the sample is set on the surface of the sample, and the sample is rotated within a plane of the surface of the sample, and thus an X-ray diffracted by a periodic structure on the surface of the sample is detected.

Since, as described above, the X-ray is focused onto the surface of the sample within the plane perpendicular to the surface of the sample, it is possible to perform measurements on reflection small-angle scattering with high resolution. It is also possible to perform accurate measurements on the two-dimensionally periodic surface microstructure by utilizing the diffraction of the X-ray. As described above, with the X-ray, it is possible to perform measurements on the microstructure on the surface of the sample.

Effects of the Invention

According to the present invention, it is possible to measure, with high resolution, the intensity of X-rays which have undergone small-angle scattering and diffraction with reflection geometry and to easily and accurately measure a microstructure on the surface of a sample.

BEST MODES FOR CARRYING OUT THE INVENTION

An embodiment of the present invention will now be described with reference to the accompanying drawings. For ease of understanding, in the drawings, like constituent elements are identified with like reference numerals, and their description will not be repeated.

[Configuration of an X-Ray Scattering Measurement Device]

(Overall Configuration)

Figure 1:
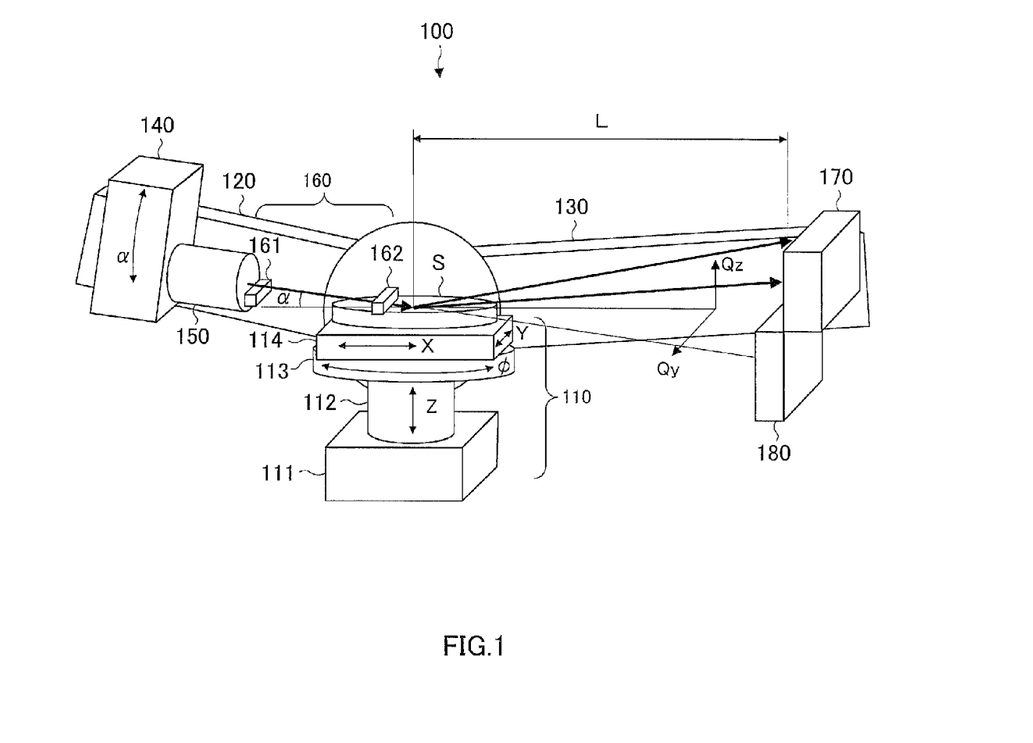
FIG. 1 is a perspective view showing the configuration of an X-ray scattering measurement device according to the present invention.

FIG. 1 is a perspective view showing the configuration of an X-ray scattering measurement device 100. As shown in FIG. 1, the X-ray scattering measurement device 100 includes a sample stage 110, arms 120 and 130, an X-ray source 140, a mirror unit 150, a slit portion 160, a two-dimensional detector 170 and a beam stop 180.

As shown in FIG. 1, the sample stage 110 supports a sample S on a flat stage, and has a fixing portion 111, an upward and downward movable portion 112, a rotary movable portion 113 and an XY stage 114. The fixing portion 111 supports and fixes the entire sample stage 110. The upward and downward movable portion 112 is coupled to the fixing portion 111, and receives an operation to move the XY stage 114 vertically in a Z-direction perpendicular to the surface of the stage (surface of the sample). Thus, it is possible to adjust the Z-position of the sample S before the irradiation of X-rays.

The rotary movable portion 113 is coupled to the upward and downward movable portion 112, and receives an operation to rotate the XY stage 114 within the surface of the stage (φ direction). This axis of rotation allows the adjustment of the direction of the sample S before the irradiation of X-rays, and also allows the rotation of the sample S during the irradiation of X-rays. Consequently, when a diffraction pattern produced by a periodic structure is measured, the intensity of scattering caused by the sample S can be measured while diffraction conditions are satisfied. The XY stage 114 is provided on the rotary movable portion 113, and can fix the sample S on the stage. By performing an operation, it is possible to move the stage in a direction (X-direction) of the line of intersection between the stage surface and an X-ray incident surface and in a direction (Y-direction) parallel to the stage surface and perpendicular to the X-direction. In this way, it is possible to adjust the position of the sample S in the XY plane before the irradiation of X-rays.

The sample S is a member that has a microstructure on its surface. For example, the X-ray scattering measurement device 100 is effective for measuring the diffraction pattern of a substrate that has a periodic structure of a nanometer size on the surface of a sample. Hence, it is possible to apply the X-ray scattering measurement device 100 to the measurements of surface structures of various devices formed with lines, spaces and dots. A pattern of small-angle scattering of a structure, other than a periodic structure, having a nanometer size may be analyzed. For example, it is possible to apply it to the measurement of nanodots formed on a silicon substrate. When the sample S has a periodic structure on its surface, the direction of the sample S within the plane is adjusted and the sample S is arranged such that the direction thereof coincides with the direction of incoming X-rays.

The arm 120 receives an operation to rotate the X-ray source 140, the mirror unit 150 and the slit portion 160 about the position of the sample, and changes the incident angle α of the X-ray with respect to the sample S. The arm 130 receives an operation to rotate the two-dimensional detector 170 about the position of the sample, and adjusts the origin position of an exit angle β. Here, with respect to the height of a structure periodically formed on the sample surface, it is also possible to determine, from data on the intensity of scattering corresponding to the exit angle β, whether variations in the density of a sidewall portion result from the inclination of the sidewall or from the unevenness thereof. As described above, it is possible to accurately identify the features of the microstructure.

The X-ray source 140 generates X-rays. The generated X-rays are incident on the sample S through the mirror unit 150 and the slit portion 160. The mirror unit 150 has two mirrors and a mirror adjustment mechanism. The two mirrors and the mirror adjustment mechanism will be described in detail later.

Although the slit portion 160 is provided to further narrow the X-rays reflected on the mirrors, it is not necessary as long as the mirrors sufficiently focus the X-rays. The slit portion 160 is formed with, for example, two collimation blocks 161 and 162; the slit portion 160 may be formed with knife edges instead of the collimation blocks. The collimation blocks 161 and 162 are formed with members capable of blocking the X-rays, and can accurately block the X-rays to enhance the accuracy of the collimation.

Figure 3:
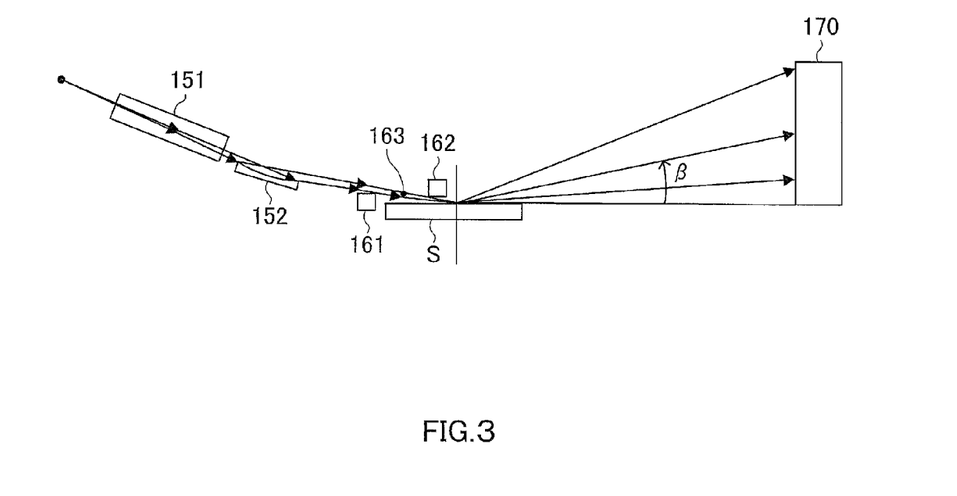
FIG. 3 is a side view showing the optical system of the X-ray scattering measurement device according to the present invention.

In order to narrow the X-rays, the collimation blocks 161 and 162 are arranged between the first mirror 152 and the sample S, and are also called a Kratky block. The bottom surface of one block is substantially parallel to the upper surface of the other block; these blocks can rotate about a pivot shaft 163 with respect to the beam. As shown in FIG. 3, the positions of the collimation blocks 161 and 162 can easily be adjusted by swinging them about the pivot shaft 163 arranged at the center between the collimation blocks. The rotation center of the collimation blocks 161 and 162 can also be a corner portion of one of the collimation blocks 161 and 162.

The two-dimensional detector 170 detects the X-rays scattered on the surface of the sample S. In the optical system of the X-ray scattering measurement device 100, a distance L from the position of the sample to the two-dimensional detector 170 is fixed. The beam stop 180 receives and blocks incident X-rays that pass through the sample S or are mirror-reflected.

(Mirrors)

Figure 2:
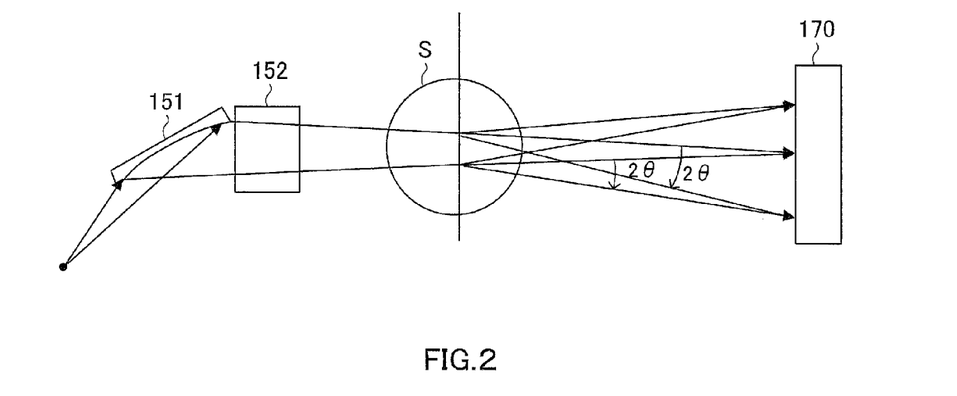
FIG. 2 is a plan view showing an optical system of the X-ray scattering measurement device according to the present invention.

Now, the basic principle of the optical system of the X-ray scattering measurement device 100 and the features of the mirrors will be described. FIG. 2 is a plan view showing the optical system of the X-ray scattering measurement device 100. FIG. 3 is a side view showing the optical system of the X-ray scattering measurement 100. In FIG. 2, the collimation blocks 161 and 162 are omitted. As shown in FIG. 2, the first mirror 151 reflects the generated X-rays within a plane parallel to the sample surface and focuses it to the two-dimensional detector 170. The X-rays scattered to form the exit angle β and a scatter angle 2θ within the plane are detected by the two-dimensional detector 170. The first mirror 151 is curved with a predetermined curvature so as to reflect the X-rays within the plane parallel to the sample surface and focus it to the two-dimensional detector 170.

As shown in FIG. 3, the second mirror 152 focuses the generated X-rays onto the sample surface within a plane perpendicular to the sample surface. The X-rays scattered to form the scatter angle 2θ are detected by the two-dimensional detector 170. The second mirror 152 is curved with a predetermined curvature so as to reflect and focus the X-rays to the sample surface.

With this configuration, the X-rays are focused to the sample surface within the plane perpendicular to the sample surface, and are focused to the two-dimensional detector 170 within the plane parallel to the sample surface. Consequently, with respect to the structure in a direction parallel to the sample surface, an image in a Qy direction can be detected with high resolution. With respect to the structure in the height direction of the sample surface, an image in a Qz direction can be detected with sufficient intensity.

The first mirror 151 is arranged in a position close to the X-ray source 140 and the second mirror 152 is arranged in a position close to the sample S so that the X-rays generated from the X-ray source 140 are reflected on the first mirror 151 and the second mirror 152 in this order and are incident on the sample S. The second mirror 152 for focusing the X-rays onto the sample surface is arranged in the position close to the sample S in this way, and it is possible to reduce a spot size on the sample surface. However, when the same effect is expected, the focusing position of the first mirror 151 and the focusing position of the second mirror 152 may be replaced with each other.

As the first mirror 151 or the second mirror 152, any one of a total reflection mirror, a multilayer mirror and a crystal plate is preferably used. The total reflection mirror is formed by curving a reflective plate or the like that is formed with a glass plate, in itself, made of Ni (nickel), Au (gold), Pt (platinum) and the like or that is formed by coating a layer of Ni (nickel) Au (gold), Pt (platinum) and the like on the surface of the glass plate.

The multilayer mirror is formed by alternately depositing layers having different electron densities on a substrate with a smooth surface a plurality of times. It is possible to effectively diffract specific X-rays such as CuKα rays by periodically repeating a multiyear structure into a plurality of layers. As a material of the substrate, a glass plate, a silicon wafer or the like is used.

With the multilayer film mirror, it is possible to change the d-spacing of the first mirror 151 or the second mirror 152 by the incident position of the X-rays. Hence, even when the incident angle α is changed, it is possible to cause diffraction by adjusting the d-spacing. Consequently, in the case where the X-rays are focused by the first mirror 151 to the two-dimensional detector 170 and the X-rays are focused by the second mirror 152 to the sample surface, it is possible to select only X-rays having the same wavelength as the specific ray (CuKα) and perform measurements with low background.

The crystal plate can be formed by using a single crystal plate such as α-SiO$_2$ (quartz), Si (silicon) or Ge (germanium). Thus, the first mirror 151 and the second mirror 152 can extract only Kα1 X-rays. Consequently, it is possible to produce X-rays having high monochromaticity and further perform detection with high resolution.

The two mirrors are used in this way, and thus it is possible to reduce the spot size of the X-rays in a direction perpendicular to the incident plane of the X-rays in the position of the samples. Consequently, it is possible to improve the resolution of the two-dimensional detector 170, and this method is suitable for microstructural measurement on the sample surface.

Figure 4:
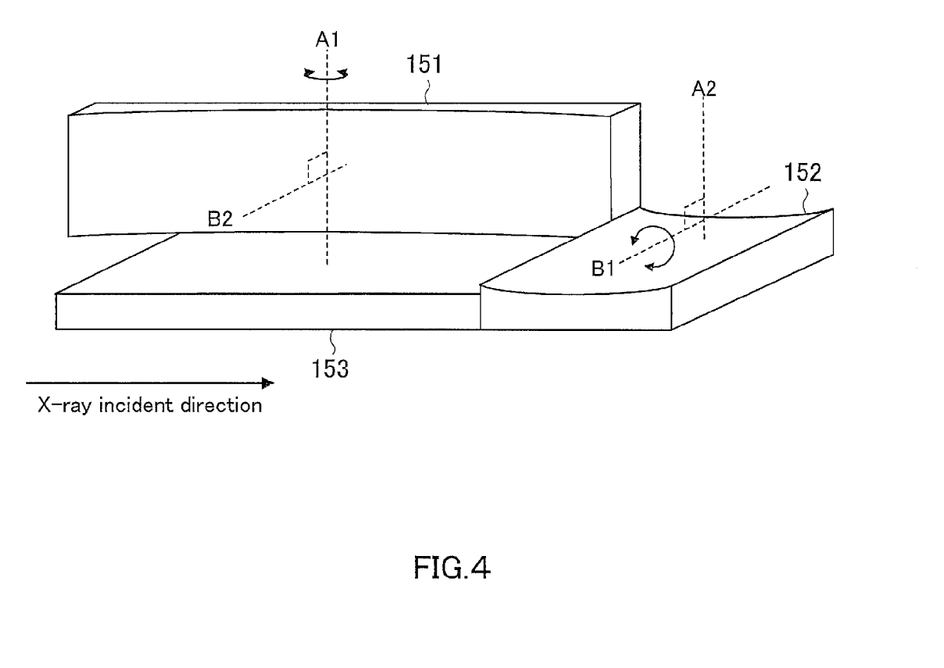
FIG. 4 is a perspective view showing the interior of a mirror unit.

Although, as described above, the first mirror 151 and the second mirror 152 are formed so as to have different focal lengths, it is necessary to perform fine adjustments on the reflection angles of the mirrors to converge the X-rays in a predetermined position at the time of use. An adjustment mechanism of mirrors having the mirror unit 150 will be described below.

(Adjustment Mechanism of Mirrors)

FIG. 4 is a perspective view showing the interior of the mirror unit 150. A mirror support portion 153 integrally supports the first mirror 151 and the second mirror 152 in a state that reflective surfaces are adjusted to be perpendicular to each other. The mirror support portion 153 changes the reflection angle of the first mirror 151, and is arranged so that it can be rotated by an axis of rotation A1 which moves the second mirror 152 in a direction perpendicular to the incident plane of the X-rays. Moreover, the mirror support portion 153 changes the reflection angle of the second mirror 152, and is arranged so that it can be rotated by an axis of rotation B1 which moves the first mirror 151 in the direction perpendicular to the incident plane of the X-rays.

In other words, the mirror support portion 153 is supported by the two axes, that is, the axis of rotation A1 and the axis of rotation B1 so that it can be rotated. The axis of rotation A1 is parallel to an axis A2 perpendicular to the surface of the second mirror 152; the axis of rotation B1 is parallel to an axis B2 perpendicular to the surface of the first mirror 151. The axis of rotation A1 is perpendicular to the axis B2; the axis of rotation B1 is perpendicular to the axis A2. Thus, when an adjustment on the first mirror 151 and an adjustment on the second mirror 152 are performed, the individual adjustments do not interfere with each other. Consequently, it is possible to independently adjust the mirrors, and this allows the corresponding operations to be easily performed. The mirrors can be displaced by pressing the ends of screws (not shown) onto the mirrors to tighten or loosen the screws. In order for the ends of the screws to be constantly in contact with the mirrors, an elastic force is applied to the mirrors. As shown in FIG. 4, the axis of rotation A1 is preferably provided in the center portion of the first mirror 151 in the X-ray incidence direction. The axis of rotation B1 is preferably provided in the center portion of the second mirror in the X-ray incidence direction.

The second mirror 152 can limit to 50 µm or less the spot size of the X-rays on the sample surface within the plane perpendicular to the sample surface. The spot size is preferably limited to 30 µm or less, and is more preferably limited to 20 µm or less. When a periodic structure of about 100 nm is measured, the spot size within the plane parallel to the sample surface is sufficient if it is about 200 µm; the spot size may be set according to the size of the two-dimensional detector 170.

[Surface Microstructure Measurement Method]

Now, a method of measuring the microstructure on the sample surface with the X-ray scattering measurement device 100 configured as described above will be described. The sample S is first placed in the sample stage 110 in consideration of the direction of the surface microstructure of the sample S. Then, the Z-position of the sample S, the position thereof in the XY plane and the orientation of the sample S are adjusted. Fine adjustments are previously performed on the first mirror 151 and the second mirror 152 so that their focal positions coincide with the two-dimensional detector and the position of the sample, respectively.

The X-rays generated from the X-ray source 140 are reflected on the first mirror 151 and the second mirror 152 in this order and are incident on the sample S. In this case, with the first mirror 151, within the plane parallel to the sample surface, the X-rays are focused onto the two-dimensional detector 170, and, with the second mirror 152, within the plane perpendicular to the sample surface, the X-rays are focused to the sample surface. Then, the X-rays scattered by irradiating the X-rays to the sample surface at a grazing angle are detected by the two-dimensional detector 170.

In this way, the intensity of the X-rays corresponding to the X-ray exit angle β and the X-ray scatter angle 2θ within the plane is measured. When the diffraction of the X-rays caused by the periodic structure is utilized, as appropriate, measurements are performed while the sample S is rotated about a Z-axis within the plane.

A small-angle scattering pattern and a diffraction pattern thus obtained include information as to a three-dimensional shape on the sample surface. For example, a parameter for identifying the shape of a unit structure of the periodic structure of the sample S is used to assume a sample model, the intensity of the X-ray scattering is calculated by simulation and fitting of the intensity of the X-ray scattering determined, based on this, from the sample model is performed on the measured intensity of the scattering. Then, as a result of the fitting, it is possible to determine the optimum value for the parameter for identifying the shape of the unit structure.

Example 1

The X-ray scattering measurement device 100 configured as described above was actually produced. In the produced X-ray scattering measurement device 100, the first mirror 151 was arranged in the position of the sample so as to focus the X-rays within the plane perpendicular to the sample surface, and the second mirror 152 was arranged in a position 400 mm away from the position of the sample so as to focus the X-rays within the plane parallel to the sample surface.

Figure 5:
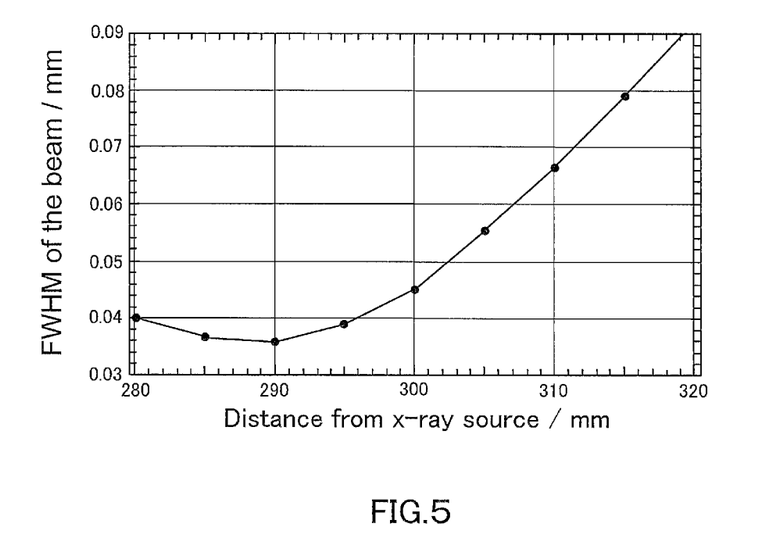
FIG. 5 is a diagram showing the relationship between a distance from an X-ray source in the position of a sample and the full width at half maximum of a beam.

Basic data on the optical system of this X-ray scattering measurement device 100 was measured. The relationship between a distance in the direction of propagation of the X-rays and the extension of the beam was measured. In this case, the measurement was performed by scanning a knife edge in a predetermined position. FIG. 5 is a diagram showing the relationship between a distance from the X-ray source 140 in the sample position and the full width at half maximum of the beam. As shown in FIG. 5, it was found that the full width at half maximum of the X-ray beam was smallest in a position 290 mm away from the X-ray source 140.

Figure 6:
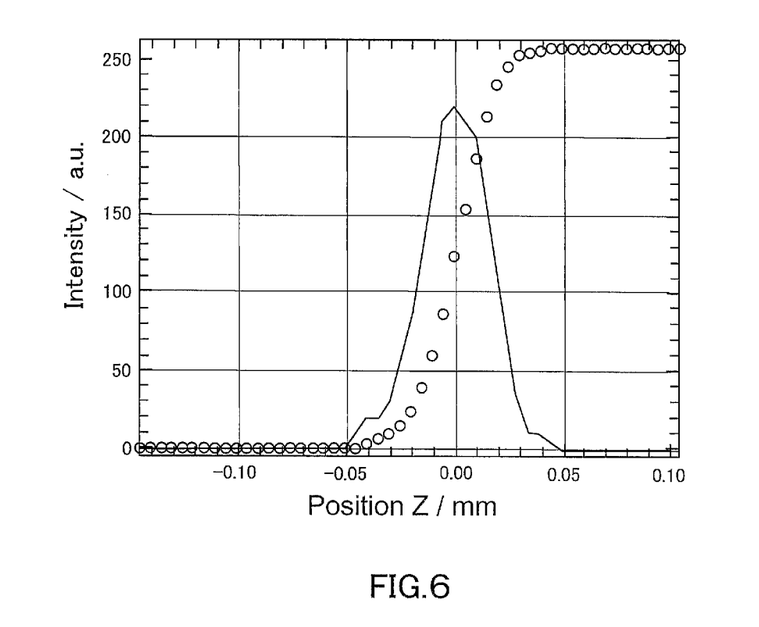
FIG. 6 is a diagram showing the relationship between a Z-position in the position of the sample and the intensity of X-ray scattering.

Moreover, in the position (focal position) 290 mm away from the X-ray source, the relationship between a position in the Z-direction and the intensity of the X-rays was measured. FIG. 6 is a diagram showing the relationship between the Z-position in the sample position and the intensity of the X-rays. As shown in FIG. 6, it was found that the full width at half maximum of the X-ray beam was about 35 µm and the X-rays are sufficiently focused.

Figure 7:
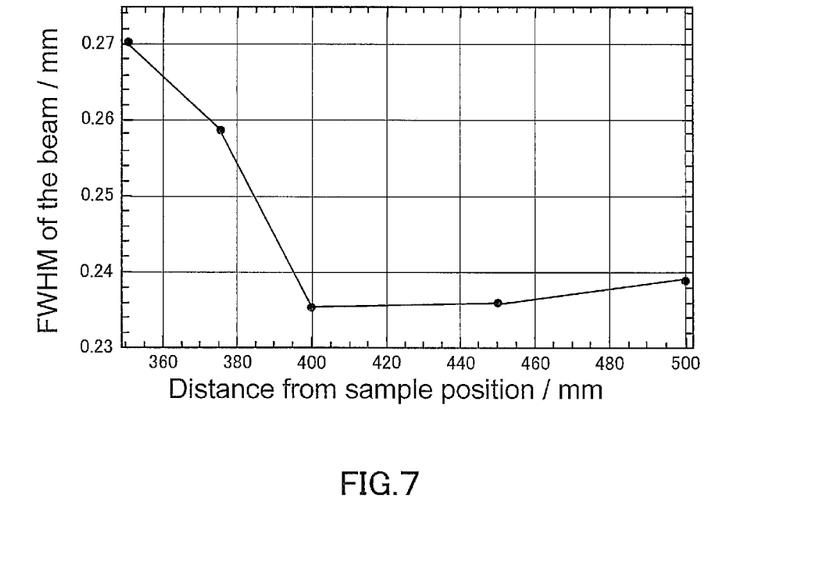
FIG. 7 is a diagram showing the relationship between the distance from the X-ray source in the position of a two-dimensional detector and the full width at half maximum of the beam.

Then, the relationship between a distance in the direction of propagation of the X-rays from the sample position and the extension of the beam was measured. FIG. 7 is a diagram showing the relationship between a distance from the sample position in the position of the two-dimensional detector and the full width at half maximum of the beam. As shown in FIG. 7, it was found that the full width at half maximum of the X-ray beam was smallest in a position 400 mm away from the sample position.

Figure 8:
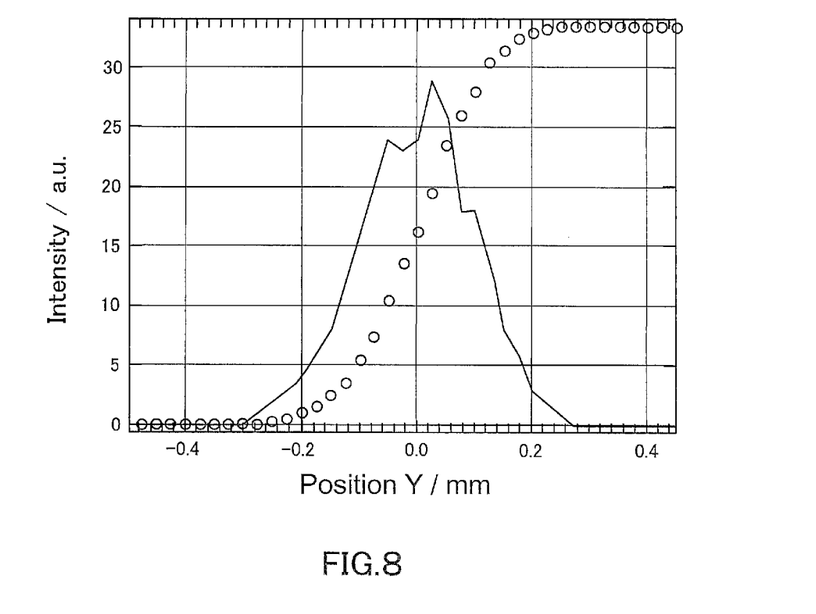
FIG. 8 is a diagram showing the relationship between a Y-position in the position of the two-dimensional detector and the intensity of the X-ray scattering.

Furthermore, in a position (focal position) 400 mm away from the sample position, the relationship between a position in the Y-direction and the intensity of the X-rays was measured. FIG. 8 is a diagram showing the relationship between the Y-position in the sample position and the intensity of the X-rays. As shown in FIG. 8, the full width at half maximum of the X-ray beam was about 230 µm. In this way, it was found that, with the first mirror 151, the X-rays are focused to the two-dimensional detector 170, and, with the second mirror 152, the X-rays are sufficiently focused to the sample surface.

Example 2

Figure 9:
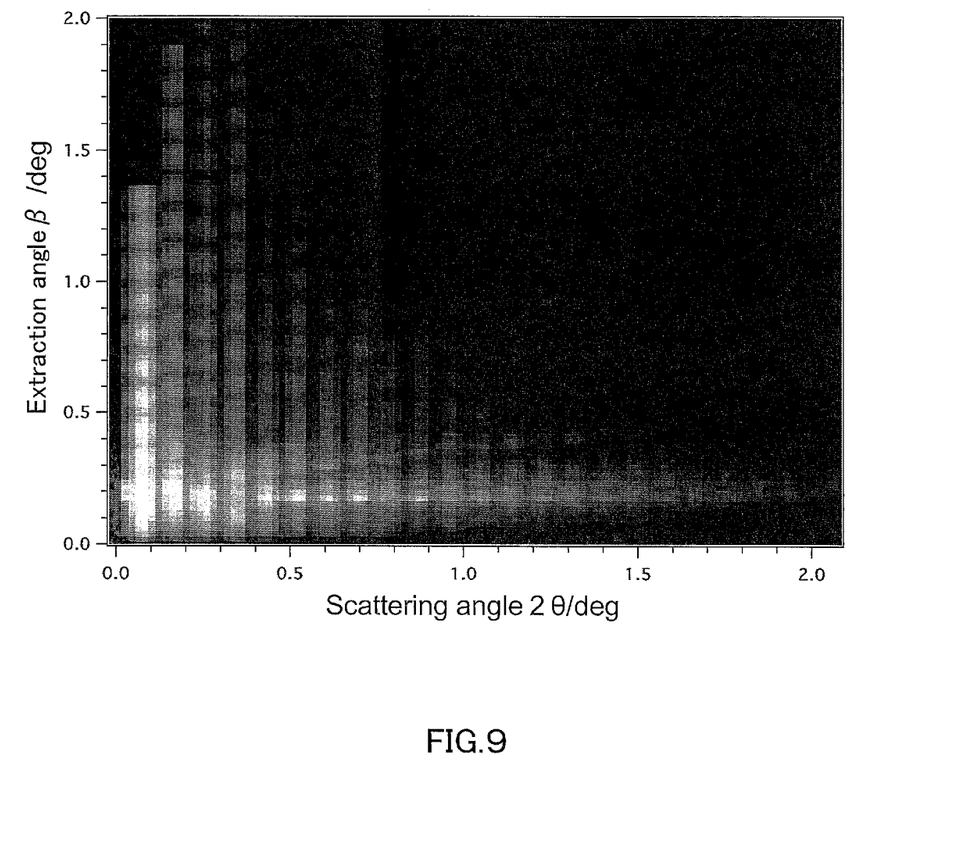
FIG. 9 is a diagram showing a diffraction pattern obtained by an experiment.

With the produced X-ray scattering measurement device 100, the X-rays were irradiated to a 100 nm-pitch grating sample on the surface of the silicon substrate at an incident angle of 0.16 degrees, and measurements were performed while the sample was rotated about the Z-axis. FIG. 9 is a diagram showing a diffraction pattern obtained by an experiment. The diffraction pattern shown in FIG. 9 is shown as data (log scale) on the two-dimensional detector 170. It was found from the diffraction pattern shown in FIG. 9 that not only a large number of peaks derived from the grating were observed in the 2θ direction within the plane but also interference fringes reflecting the height of the grating were observed in the exit angle β direction. The data is analyzed, and thus it is possible to measure the two-dimensional cross section of the grating without the grating being destroyed.

DESCRIPTION OF SYMBOLS

100 X-ray scattering measurement device
110 Sample stage
111 Fixing portion
112 Upward and downward movable portion
113 Rotary movable portion
114 XY stage
120 and 130 Arms
140 X-ray source
150 Mirror unit
151 First mirror
152 Second mirror
153 Mirror support portion
160 Slit portion
161 and 162 collimation blocks
163 Pivot shaft
170 Two-dimensional detector
180 Beam stop
A1 Axis of rotation
B1 Axis of rotation
A2 Axis parallel to the axis of rotation A1
B2 Axis parallel to the axis of rotation B1
S Sample

The invention claimed is:

1. An X-ray scattering measurement device suitable for microstructural measurement on a surface of a sample, said device comprising:
an X-ray source that generates an X-ray;
a first mirror that reflects said generated X-ray;
a second mirror that reflects said X-ray reflected by said first mirror;
a sample stage that supports said sample to which said X-ray reflected by said second mirror is irradiated; and
a two-dimensional detector that detects said X-ray scattered on said surface of said sample,
wherein said first mirror focuses said generated X-ray onto said two-dimensional detector within a plane parallel to said surface of said sample, and
said second mirror focuses said X-ray reflected by said first mirror onto said surface of said sample within a plane perpendicular to said surface of said sample.

2. The X-ray scattering measurement device of claim 1, further comprising:
a mirror support portion that arranges and integrally supports said first mirror and second mirror such that reflective surfaces thereof are perpendicular to each other,
wherein said mirror support portion is provided so as to be able to rotate about two axes: an axis of rotation which changes a reflection angle of said X-ray by said first mirror and moves said second mirror in a direction perpendicular to an incident plane of the X-ray; and an axis of rotation which changes a reflection angle of said X-ray by said second mirror and moves said first mirror in a direction perpendicular to an incident plane of the X-ray.

3. The X-ray scattering measurement device of claim 1, wherein said second mirror can limit to 50 μm or less a spot size of said X-ray on said surface of said sample in a direction perpendicular to said surface of said sample.

4. The X-ray scattering measurement device of claim 1, wherein said sample stage is provided so as to be rotatable to change an incident angel of said generated X-ray to said surface of said sample and to be rotatable within a plane of said surface of said sample.

5. The X-ray scattering measurement device of claim 1, wherein said first or second mirror is a multilayer mirror.

6. The X-ray scattering measurement device of claim 1, wherein said first or second mirror is formed with a crystal plate.

7. The X-ray scattering measurement device of claim 1, further comprising:
a pair of collimation blocks in an X-ray passage portion between said second mirror and said sample.

8. An X-ray scattering measurement device suitable for microstructural measurement on a surface of a sample, said device comprising:
an X-ray source that generates an X-ray;
a first mirror that reflects said generated X-ray;
a second mirror that reflects said X-ray reflected by said first mirror;
a sample stage that supports said sample to which said X-ray reflected by said second mirror is irradiated; and
a two-dimensional detector that detects said X-ray scattered on said surface of said sample,
wherein said first mirror focuses said generated X-ray onto said surface of said sample within a plane perpendicular to said surface of said sample, and
said second mirror focuses said X-ray reflected by said first mirror onto said two-dimensional detector within a plane parallel to said surface of said sample.

9. The X-ray scattering measurement device of claim 8, further comprising:
a mirror support portion that arranges and integrally supports said first mirror and second mirror such that reflective surfaces thereof are perpendicular to each other,
wherein said mirror support portion is provided so as to be able to rotate about two axes: an axis of rotation which changes a reflection angle of said X-ray by said first mirror and moves said second mirror in a direction perpendicular to an incident plane of the X-ray; and an axis of rotation which changes a reflection angle of said X-ray by said second mirror and moves said first mirror in a direction perpendicular to an incident plane of the X-ray.

10. The X-ray scattering measurement device of claim 8, wherein said first mirror can limit to 50 μm or less a spot size of said X-ray on said surface of said sample in a direction perpendicular to said surface of said sample.

11. The X-ray scattering measurement device of claim 8, wherein said sample stage is provided so as to be rotatable to change an incident angel of said generated X-ray to said surface of said sample and to be rotatable within a plane of said surface of said sample.

12. The X-ray scattering measurement device of claim 8, wherein said first mirror or second mirror is a multilayer mirror.

13. The X-ray scattering measurement device of claim 8, wherein said first mirror or second mirror is formed with a crystal plate.

14. The X-ray scattering measurement device of claim 8, further comprising:
- a pair of collimation blocks in an X-ray passage portion between said second mirror and said sample.

15. An X-ray scattering measurement method suitable for microstructural measurement on a surface of a sample, said method comprising the steps of:
- reflecting an X-ray generated by an X-ray source with a first mirror;
- reflecting said X-ray reflected by said first mirror with a second mirror;
- making said X-ray reflected by said second mirror incident on said sample; and
- detecting said X-ray scattered on said surface of said sample with a two-dimensional detector,
- wherein said first mirror focuses said generated X-ray and said second mirror focuses said X-ray reflected by said first mirror, and a focusing position within a plane parallel to said surface of said sample is set on said two-dimensional detector and a focusing position within a plane perpendicular to said surface of said sample is set on said surface of said sample, and thus an X-ray scattered at a small angle on said surface of said sample is detected.

16. An X-ray scattering measurement method suitable for microstructural measurement on a surface of a sample, said method comprising the steps of:
- reflecting an X-ray generated by an X-ray source with a first mirror;
- reflecting said X-ray reflected by said first mirror with a second mirror;
- making said X-ray reflected by said second mirror incident on said sample; and
- detecting said X-ray scattered on said surface of said sample with a two-dimensional detector,
- wherein said first mirror focuses said generated X-ray and said second mirror focuses said X-ray reflected by said first mirror, and a focusing position within a plane parallel to said surface of said sample is set on said two-dimensional detector and a focusing position within a plane perpendicular to said surface of said sample is set on said surface of said sample, and said sample is rotated within a plane of said surface of said sample, and thus an X-ray diffracted by a periodic structure on said surface of said sample is detected.

* * * * *